(12) United States Patent
Wolff et al.

(10) Patent No.: US 9,566,432 B2
(45) Date of Patent: Feb. 14, 2017

(54) DEVICE AND METHOD FOR STIMULATING SALIVATION

(76) Inventors: Andy Wolff, Harutzim (IL); Ben Zion Beiski, Kiryat-Ono (IL)

( * ) Notice: Subject to any disclaimer, the term of this patent is extended or adjusted under 35 U.S.C. 154(b) by 999 days.

(21) Appl. No.: 12/795,421

(22) Filed: Jun. 7, 2010

(65) Prior Publication Data

US 2010/0312311 A1    Dec. 9, 2010

Related U.S. Application Data

(60) Provisional application No. 61/217,978, filed on Jun. 8, 2009.

(51) Int. Cl.
     *A61N 1/05*      (2006.01)
     *A61N 1/36*      (2006.01)

(52) U.S. Cl.
     CPC ......... *A61N 1/36014* (2013.01); *A61N 1/0548* (2013.01)

(58) Field of Classification Search
None
See application file for complete search history.

(56) References Cited

U.S. PATENT DOCUMENTS

| | | | | |
|---|---|---|---|---|
| 3,855,701 A | * | 12/1974 | Le Clair | 433/7 |
| 4,519,400 A | * | 5/1985 | Brenman et al. | 600/554 |
| 2005/0090864 A1 | * | 4/2005 | Pines et al. | 607/2 |

FOREIGN PATENT DOCUMENTS

WO    WO 2006008741 A1 * 1/2006

OTHER PUBLICATIONS

Strietzel, F.P. et al. Oral Diseases 13:206-213 (2007).*
Karaman, A.I. et al. Am. J. Orthod. Dentofacial Orthop. 124:327 (2003).*

* cited by examiner

*Primary Examiner* — Diana B Johannsen
(74) *Attorney, Agent, or Firm* — Pearl Cohen Zedek Latzer Baratz LLP

(57) ABSTRACT

Embodiments of the invention provide a reusable intra-oral device for treating xerostomia. The device having a structure adaptable for oral cavities of multiple users. The hermitically sealed housing comprises of an electronic module having a signal generator configured to generate electrical signals based on one or more values of one or more predefined parameters. Further, the device comprises of electrodes connected to the electronic module. The electrodes are configured to apply the electric signals for stimulating lingual nerves in the oral cavities to induce salivation.

14 Claims, 11 Drawing Sheets

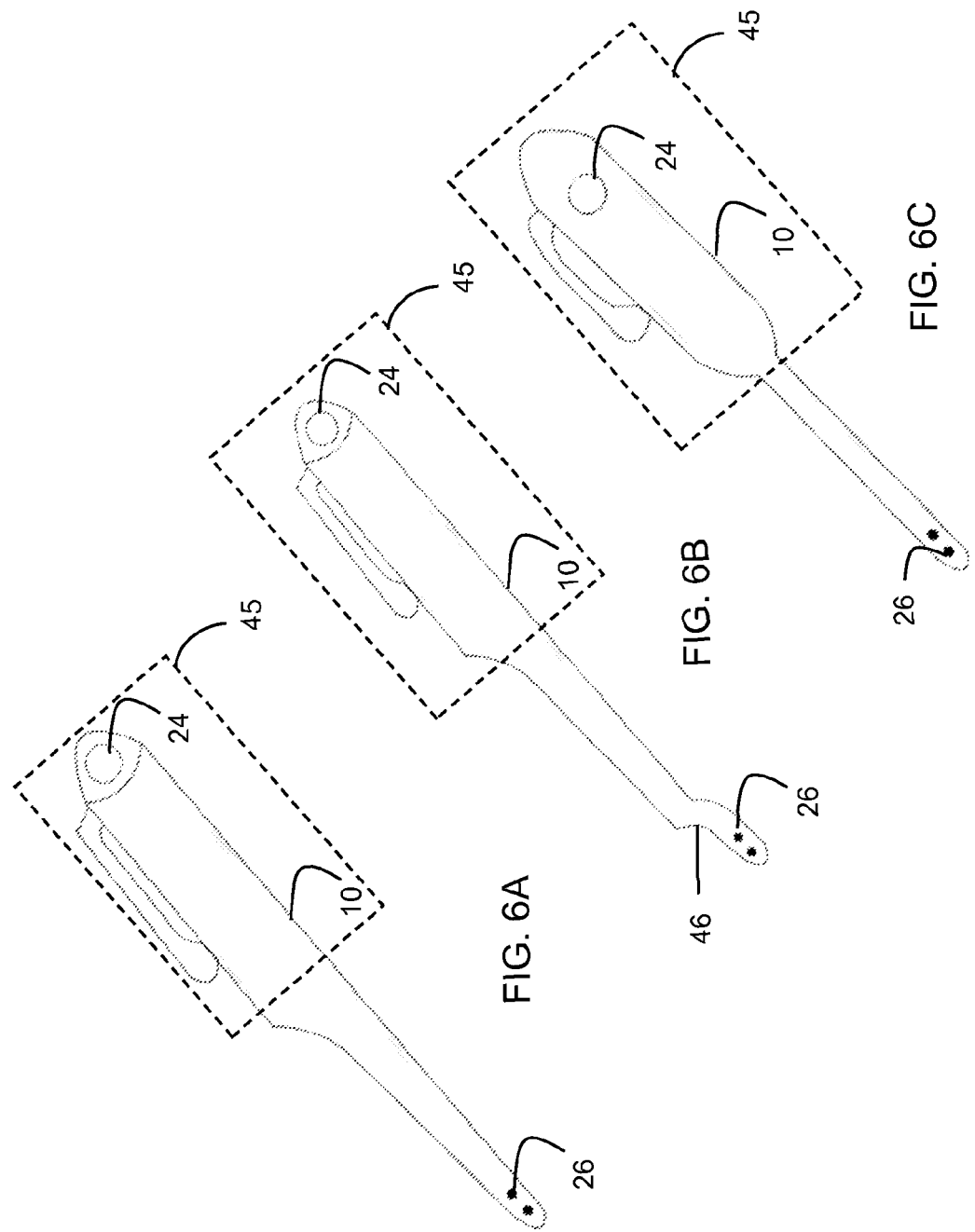

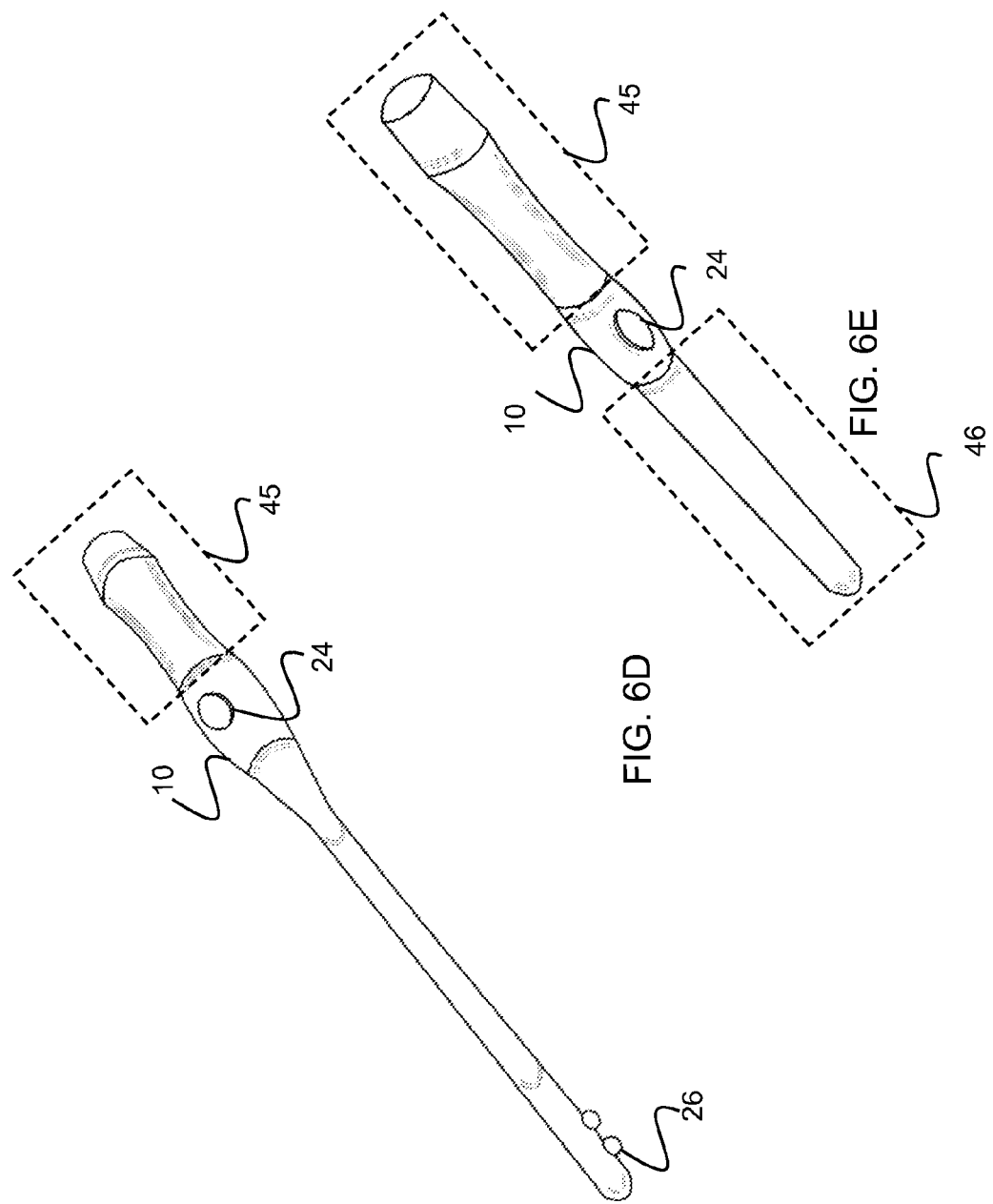

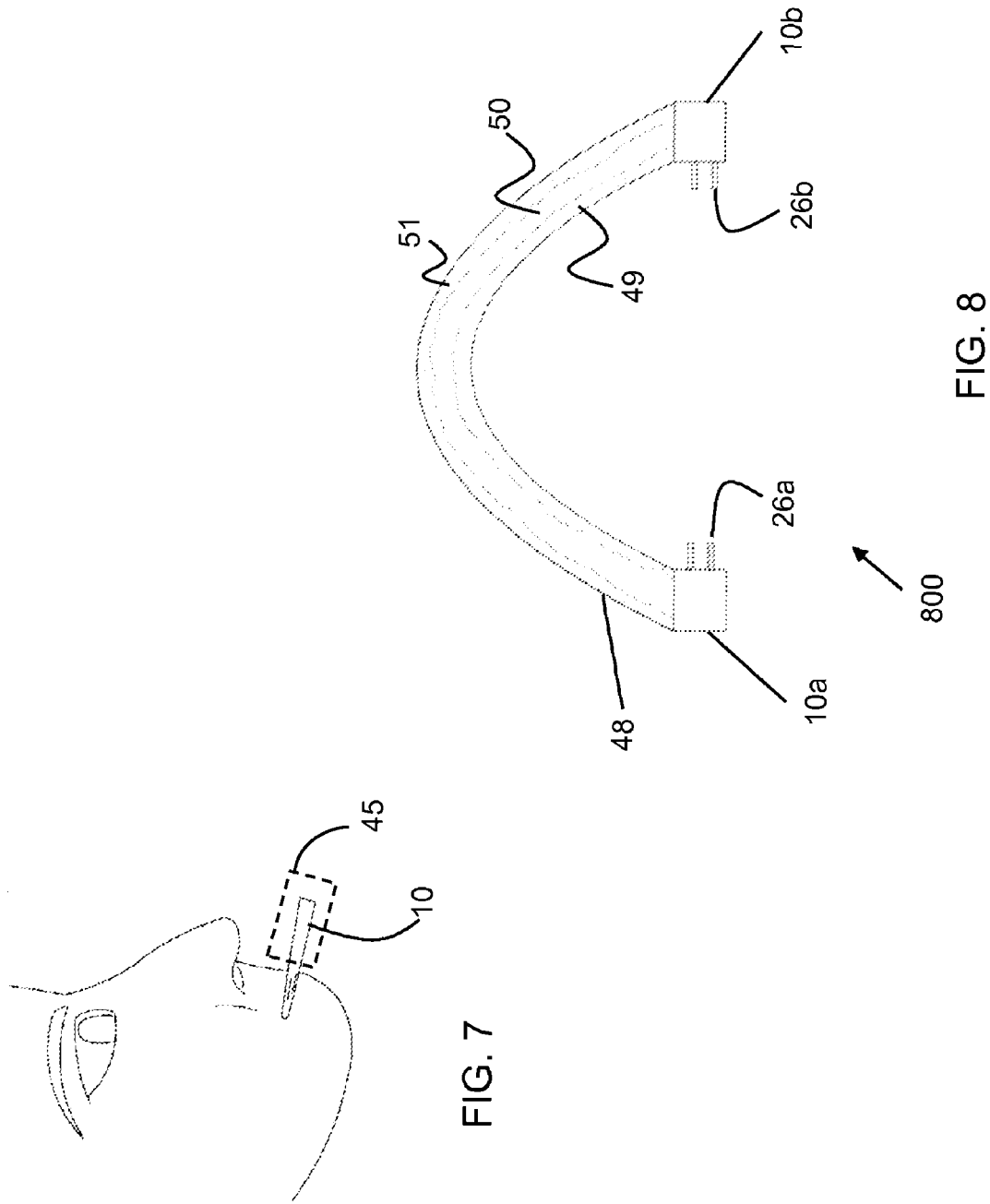

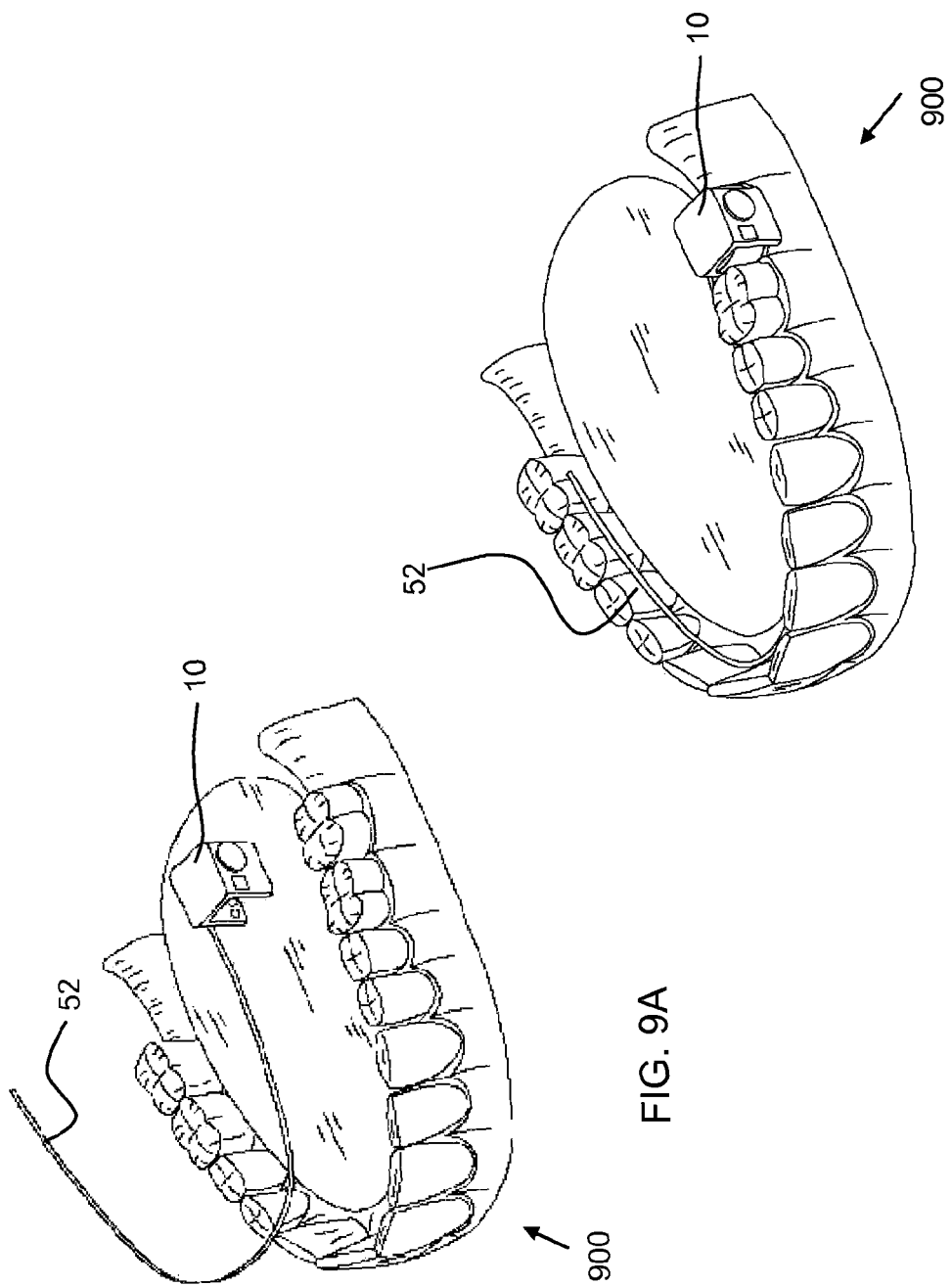

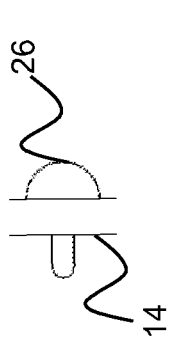
FIG. 10E
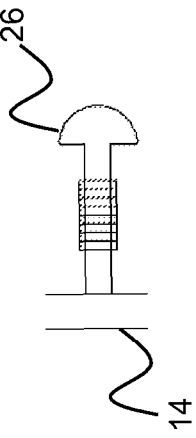
FIG. 10F
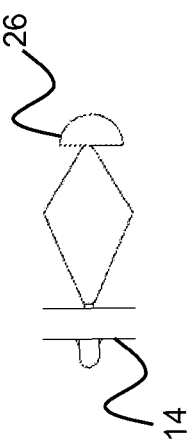
FIG. 10G
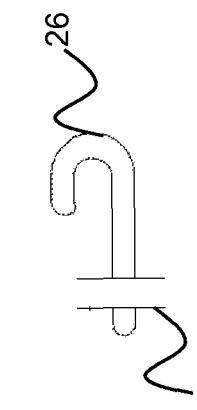
FIG. 10A
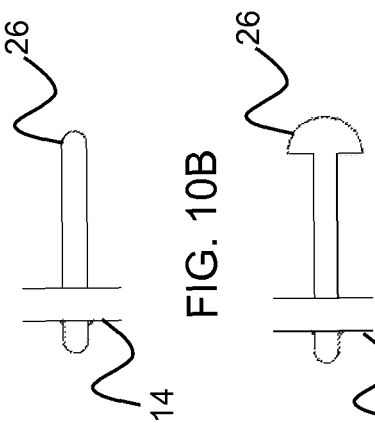
FIG. 10B
FIG. 10C
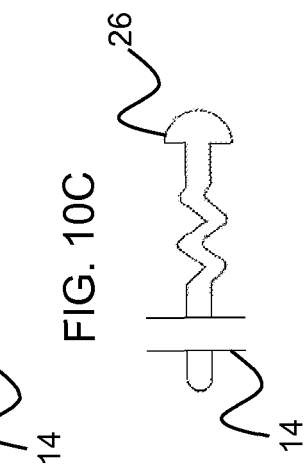
FIG. 10D

DEVICE AND METHOD FOR STIMULATING SALIVATION

CROSS REFERENCE TO RELATED APPLICATION

This application claims the benefit of U.S. Provisional Patent Application No. 61/217,978, filed Jun. 8, 2009.

FIELD OF THE INVENTION

The present invention relates to a device and method for stimulating salivation. More particularly, the invention relates to a device and method for promoting the production of saliva by electrical stimulation inside the oral cavity of a user.

BACKGROUND OF THE INVENTION

Saliva is a clear liquid secreted into the mouth by various glands and is essential for maintenance of oral function and health and performs various critical functions in the oral cavity. For example, saliva neutralizes the acids that promote dental caries and helps in the re-mineralization of areas of incipient caries development. Further, saliva contains specific antimicrobial agents that assist in reducing the number of bacteria in the oral cavity by several means, such as dilution, aggregating factors, microbicidal enzymes and so forth. Moreover, salivary glycoproteins reduce intraoral friction between different oral structures such as teeth, cheek, tongue and lips by lubricating the hard and soft tissues. Also, saliva aids in swallowing by facilitating bolus formation, and salivary enzymes such as lipase and amylase start the digestion of food. Moreover, perception of taste is facilitated by salivary dilution.

Saliva is produced by the salivary glands. Every normal human has three pairs of major salivary glands: the parotid glands that are located under the skin of the cheeks, the submandibular glands and the sublingual glands, which are located at the bottom of the mouth. In addition, hundreds of minor salivary glands are spread throughout the oral cavity lining. According to C. Dawes in "The contribution of oral minor mucous gland secretions to the volume of whole saliva in man", Archs Oral Biology, 1973, the parotid, submandibular and sublingual salivas comprise more than 90% of the whole saliva present in the mouth. The secretion of saliva is regulated by the salivary reflex that is part of the autonomic nervous system of body. Afferent fibers that are part of cranial nerves carry various signals such as those for tasting, chewing or perceiving a foreign body from the oral cavity to the brain. In response to the signals, efferent fibers that run through the same or others nerves, release stimulatory commands to all salivary glands. This phenomenon is known as 'salivary reflex'. The only nerve exposed to the oral cavity lining that carries both types of fibers (afferent and efferent) is the lingual nerve. The lingual nerve directly stimulates the submandibular glands and the sublingual glands. Further, the lingual nerve indirectly stimulates all salivary glands through the salivary reflex.

Xerostomia or dry mouth symptom is a very common problem. According to estimates, about 10% of the adult population over 25 years of age may complain of it at some time, and it is a serious health and quality of life problem for about 1-2% of the adult population. Typically, xerostomia may be associated with salivary gland dysfunction. However, xerostomia may not always reflect the actual salivary gland performance. See "Xerostomia: evaluation of a symptom with increasing significance", Journal of American Dental Association, 1985, Philip C. Fox et al. According to Wolff A et al, in "Major salivary gland output differs between users and non-users of specific medication categories", Gerodontology, 2008, xerostomia is more closely related to the function of the submandibular and sublingual glands than the parotid glands. Chronic xerostomia can be caused by diseases such as Sjögren's syndrome, nerve damage, certain medications, therapeutic irradiation and or by other chronic diseases. Xerostomia can cause difficulty in eating dry foods, swallowing, speaking and wearing dentures. Moreover, xerostomia increases the number of wake-up episodes during sleeping time in a need to moist the mouth, susceptibility to dental caries, oral pain and frequent infections.

Generally, the treatment of xerostomia is difficult and the currently available treatments are not satisfactory. Symptomatic treatments include mouthwashes, gels and local intra-oral sialogogues (salivation stimulators) such as sugarless hard candies or chewing gum. However, such treatments provide only short-lasting effects that fade after a few minutes of treatment. Further, in case of patients having xerostomia due to a non-pharmacologic cause, ingested systemic sialogogues (if not contraindicated) may be helpful. However, ingested systemic sialogogues have adverse effects such as perspiration, flushing, urinary urgency and lacrimation.

It is well known that stimulation of the autonomic nerves associated with the salivary glands by low power electric stimulation can increase salivation output of the salivary glands. Furthermore, due to the dual type of fibers carried by the lingual nerve (afferent and efferent), stimulating the vicinity of this nerve, i.e. the mucosa behind the lower third molar, results in both, (a) direct impulses to the submandibular glands and the sublingual glands nerve, and (b) indirect stimulus through the salivary reflex to the other major and minor salivary glands in the oral and pharyngeal regions. As a result, the salivation is increased (see, "Electrostimulating device in the management of xerostomia", Oral Diseases, 2007, Strietzel FP et al.). Placing a module, or part of it, inside the intra-oral environment to provide electric stimulation requires unique manufacturing methods in order to guarantee the functionality and durability of the device over time. Generally, any object placed within the oral cavity must withstand constant wetness (of saliva and intake liquids), mastication forces, forces applied by the tongue and other oral muscles, varying pH levels from 1 to 9, ambient temperature of 37° C., and temperature variations ranging between +0° C. and +65° C. due to cold and hot drinks intake.

Existing techniques as disclosed in U.S. Pat. Nos. 4,519,400 and 4,637,405 assigned to Brenman et al., teach a stimulator for inducing salivation by neural stimulation. The stimulator includes a housing that encloses electronic signal generating means and electrodes for applying a signal to neurally sensitive areas of the oral cavity to induce salivation. The stimulator is coupled to the hard palate of a user and is held in place by connecting it to a tooth of the upper jaw. However, this configuration causes discomfort to the user. Further, the user's ability to speak, eat and/or drink are affected severely. Moreover, the signals do not stimulate the lingual nerve.

Another existing technique as disclosed in EP Pat Application No. 278,847 assigned to Jaffreo Albert, teaches the application of an electrical signal to neurally sensitive locations by an apparatus. The apparatus is in the form of a pellet made of a non-conductive material with electrodes on the opposite faces of the apparatus. The apparatus has no means of firm attachment within the oral cavity and is only held freely within the pral cavity. Further, the apparatus can be moved from one place to another in the oral cavity by aid of the tongue. However, there is a risk that the apparatus may be accidentally swallowed into the gastro-intestinal tract or aspirated into the lungs by the user.

Yet another existing technique as disclosed in U.S. Pat. No. 6,230,052 assigned to Wolff et al. teaches an implantable device for inducing salivation by neural stimulation at neurally sensitive location within an oral or perioral tissue of the user. The device includes a housing adapted to be permanently implanted within the oral or perioral tissue. The housing includes an enclosure for engaging an electrical signal generator. Further, the signal generator includes a power source and electrodes. The electrodes form an electrical contact with neurally sensitive location of the oral or perioral tissue, the stimulation of which by electrical energy can induce salivation. However, the device needs to fixed by an invasive procedure, requiring implantation as essential component in the oral cavity. Moreover, the implant is a costly component and requires a surgical procedure involving considerable risk to the user.

Another existing technique as disclosed in U.S. Pat. No. 7,477,947 assigned to Pines et al. teaches electrical detection of a lack of saliva in the oral cavity and electrically stimulating the oral cavity to induce the production of saliva from the salivary glands. However, electric detection and measurement of saliva quantity and oral moisture and comparing the obtained measure to a moisture limit value are essential elements needed to deliver the electrical impulses. An additional limitation of this patent is the need of the intraoral device to be configured so as to be fixable to at least one tooth within an oral cavity of an individual.

Yet another existing technique as disclosed in PCT Pat. Application No. WO 2006/100238 to Michel Rochat et al., teaches a salivary stimulation device having an electronic circuit that generates and transmits electric signals by means of stimulation electrodes. The aforementioned device takes the form of a channel that is preferably made of a transparent thermoplastic material. The electronic circuit is embedded at one edge of the channel. According to the invention, only the free ends of the electrodes extend outwardly from the channel in order to be brought into contact with the oral cavity and to stimulate the salivary glands of the user. However, the device may be specially designed for the oral cavity of the user. An existing technique for manufacturing and testing of intra-oral embedded devices is disclosed in U.S. Pat. Application No. 2009/0210032.

In light of the above discussion, techniques are desired for treating xerostomia devoid of the above limitations.

SUMMARY

According to an aspect of the invention, a reusable intra-oral device for treating xerostomia is provided. The device having a structure adaptable for oral cavities of one or more users, and configured to be inserted and removed one or more times from the oral cavities.

According to another aspect of the invention there is provided a reusable intra-oral device for treating xerostomia. The device having a structure adaptable for oral cavities of one or more users and the device comprises a hermetically sealed housing. The housing comprises an electronic module having a signal generator configured to generate electrical signals based on one or more values of one or more predefined parameters. Further, the device comprises electrodes connected to the electronic module. The electrodes are configured to apply the electric signals for stimulating lingual nerves in the oral cavities to induce salivation.

According to yet another aspect of the invention there is provided a method for treating xerostomia. The method comprising: (a) providing a reusable intra-oral device for treating xerostomia, the device having a structure adaptable for oral cavities of one or more users, the device comprising a hermetically sealed housing, the housing comprising an electronic module having a signal generator configured to generate electrical signals based on one or more values of one or more predefined parameters, and a plurality of electrodes connected to the electronic module, wherein the electrodes are configured to apply the electric signals for stimulating lingual nerves in the oral cavities to induce salivation; and (b) placing said device in the oral cavities.

According to still another aspect of the invention there is provided a system for treating xerostomia, the system having a structure that is adaptable for oral cavities of one or more users, the system comprising: (a) a lingual bar; and (b) a reusable intra-oral device comprising: (i) at least one hermetically sealed housing coupled to the lingual bar, the housing comprising an electronic module having a signal generator configured to generate electrical signals based on one or more values of one or more predefined parameters; and (ii) a plurality of electrodes connected to the electronic module, wherein the electrodes are configured to apply the electric signals for stimulating lingual nerves in the oral cavities to induce salivation.

According to further features of the invention the device has an extra-oral component configured to protrude outside the oral cavities, which houses the power supply, the signal generator and other supporting circuitry.

According to still further of the invention the power source is a battery.

According to still further features of the invention the attachment element is adapted so that the device is capable of being repeatedly inserted and removed from the oral cavity.

According to still further features of the invention the signal generator produces electrical impulses. The impulses may have intensity between one microampere and 1000 microamperes.

According to still further features of the invention, the electrodes may be located to touch the lingual side close to the lower third molar site, in proximity to the lingual nerve.

According to still further features of the invention, the device is structured as a lingual bar.

According to still further features of the invention, the device is structured as an elongated bar.

According to still further features of the invention, the device is structured as a boil and bite mouthpiece.

According to still further features of the invention, the device is structured as a dental clasp.

According to still further features of the invention, the device includes a switch to turn on and off the device, and to increase or decrease stimulus intensity by changing parameters such as amperage, voltage, frequency and duty cycle.

According to still further features of the invention, the structure of the device and the electronic module comprises a bio-compatible material.

According to still further features of the invention, the material of the housing comprises a vinyl, silicone, acrylate, ceramic, polymers, metal, metal alloys or other dental material, or any combination thereof, in such a way that the electronic module and/or the power source remain embedded.

According to still further of the invention, the material of electrodes may be bio-compatible.

According to still further features of the invention, the electrodes surface may be finished with electropolish, coated with polymers, plated with gold, platinum-iridium alloy silver, nickel, platinum, silver, silver-oxide, copper, titanium oxide or any combination thereof.

According to still further features of the invention, the electronic module and/or power source may be coated with a protective coating such as parylene, a conformal coating, such as silicone, anti-bacterial coating, silver, silver-oxide, dental resins, nano particles, or any combination thereof prior to embedding it between the layers.

According to still further features of the invention, the device includes a wetness sensor configured to sense the intra-oral wetness level.

According to still further features in the described preferred embodiments, the signal generator includes a mechanism for producing a series of pulses series having amplitude of about half to ten volts, a pulse width of about 1-1000 microseconds and a frequency of about 1-160 Hz. Further, the impulses may be uni-polar or bi-polar pulses.

According to still further features in the described preferred embodiments, the device is provided with a display to present the stimulation level in both numeric and alphanumeric characters.

The present invention successfully addresses the shortcomings of the presently known configurations by providing a device for inducing salivation which can be inserted and removed freely and safely into and from the oral cavity, to therefore eliminate the discomfort, risk and inconvenience associated with using the prior art devices, which are placed in the oral cavity.

According to still further features in the described preferred embodiments, the distance between the electrodes may range from 1 millimeter to 15 millimeter.

BRIEF DESCRIPTION OF THE DRAWINGS

Figure 1:
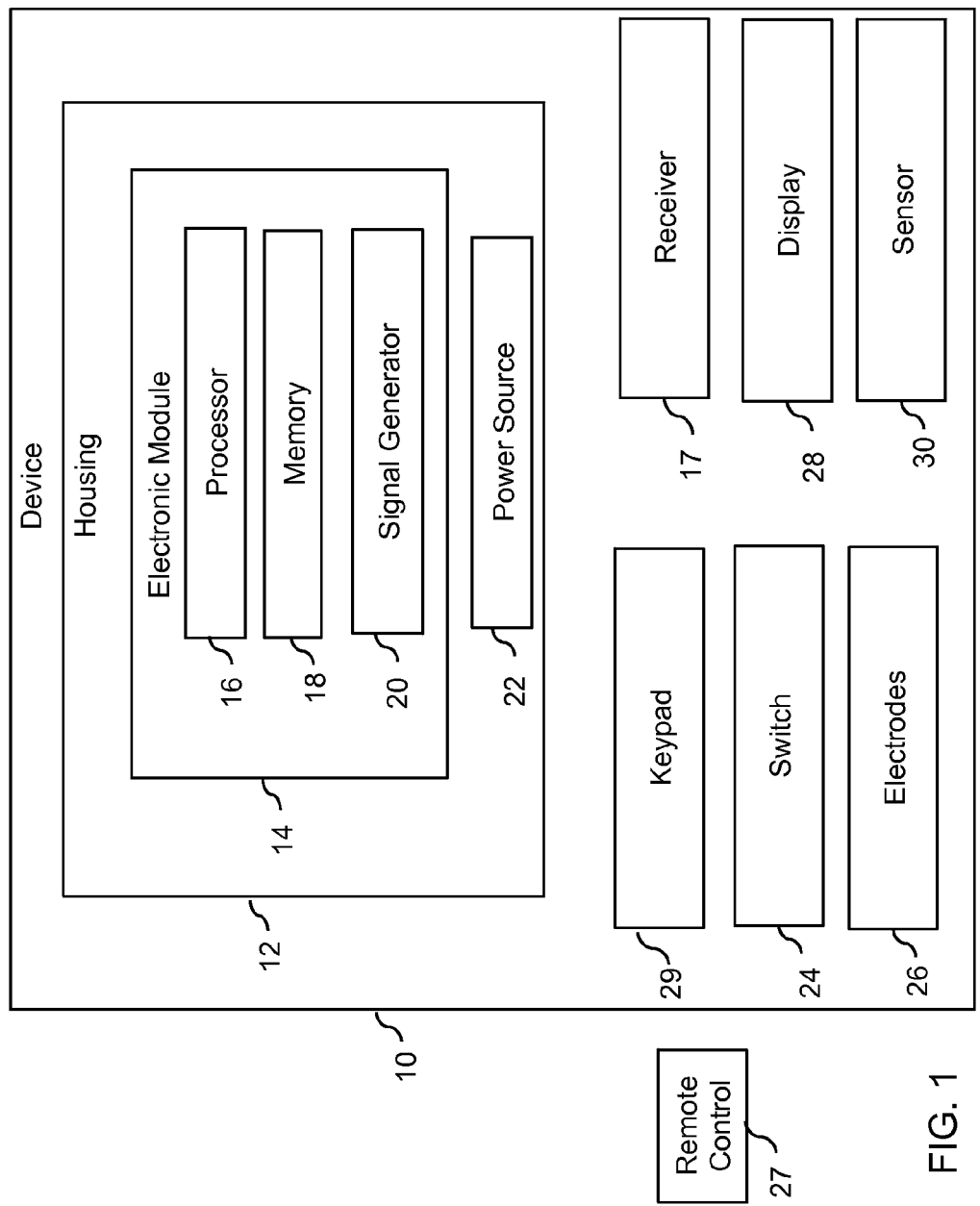
Figure 2:
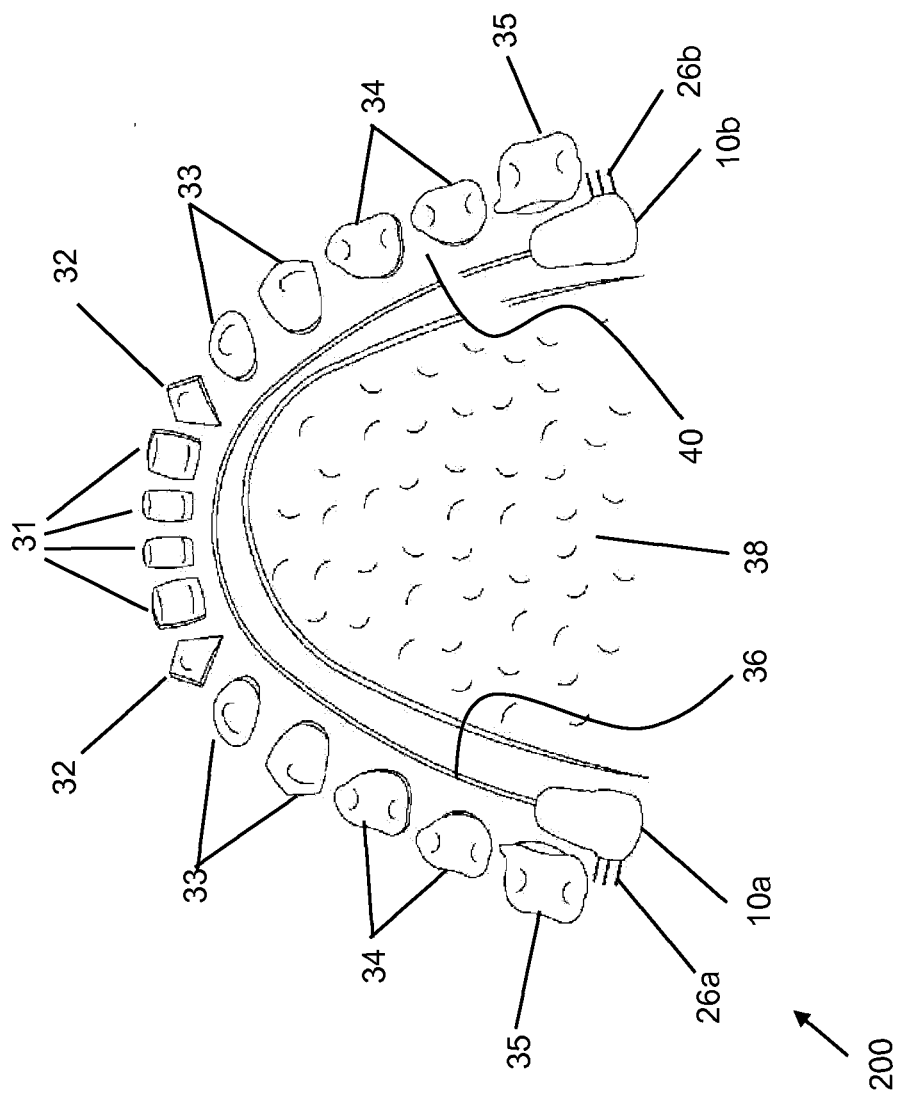
Figure 3:
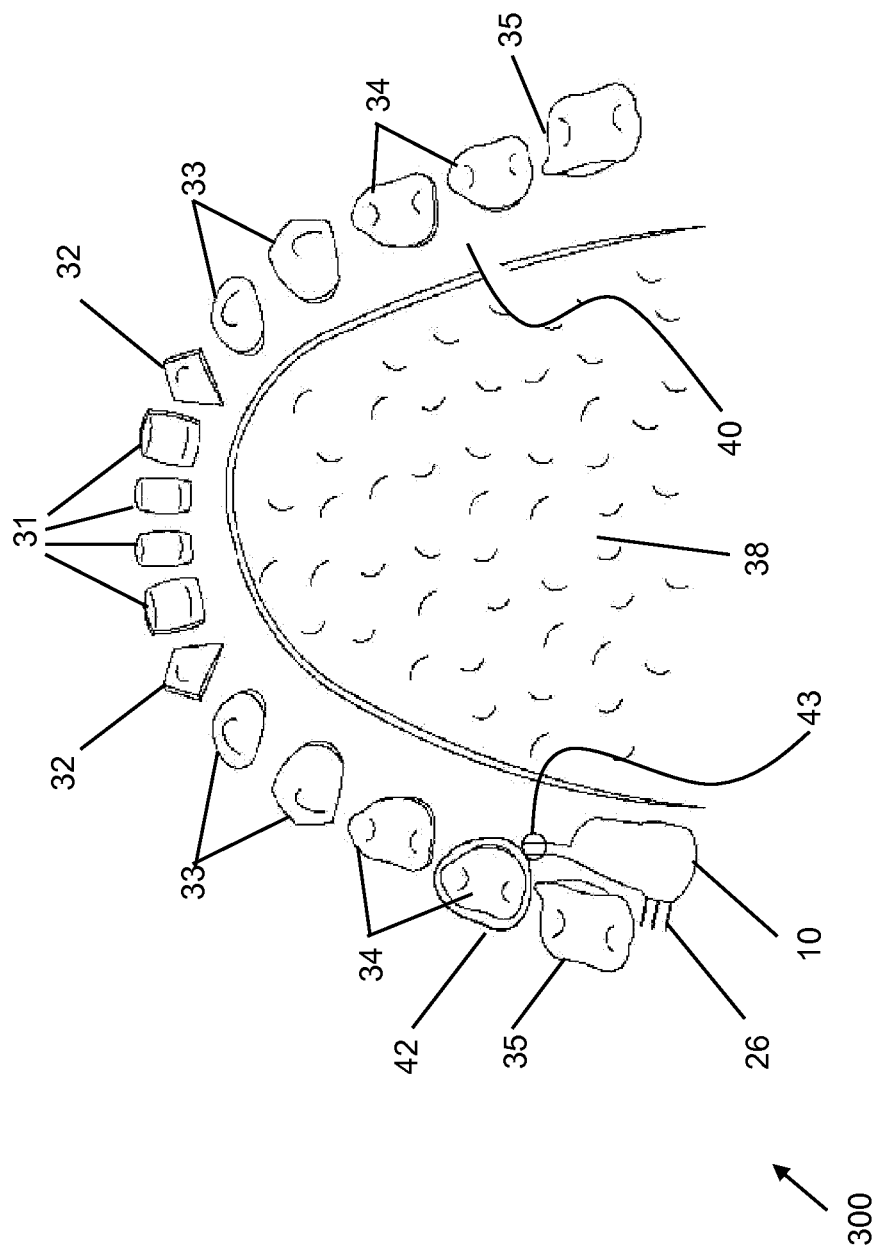
Figure 4:
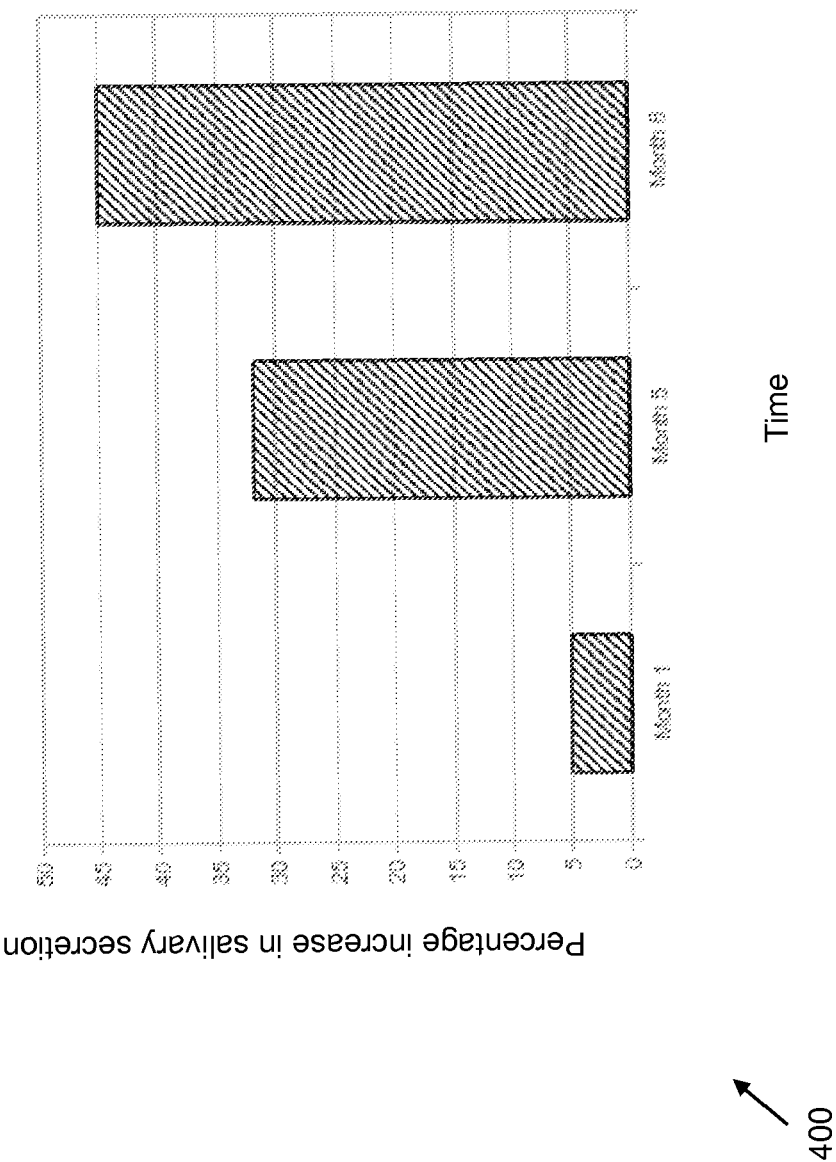
Figure 5:
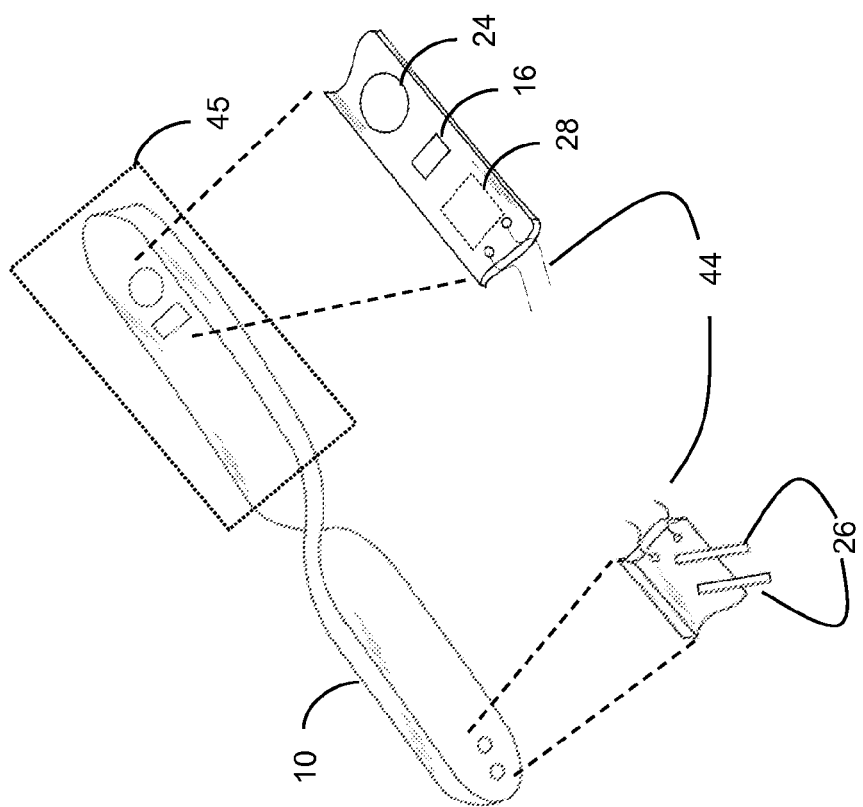
Figure 11:
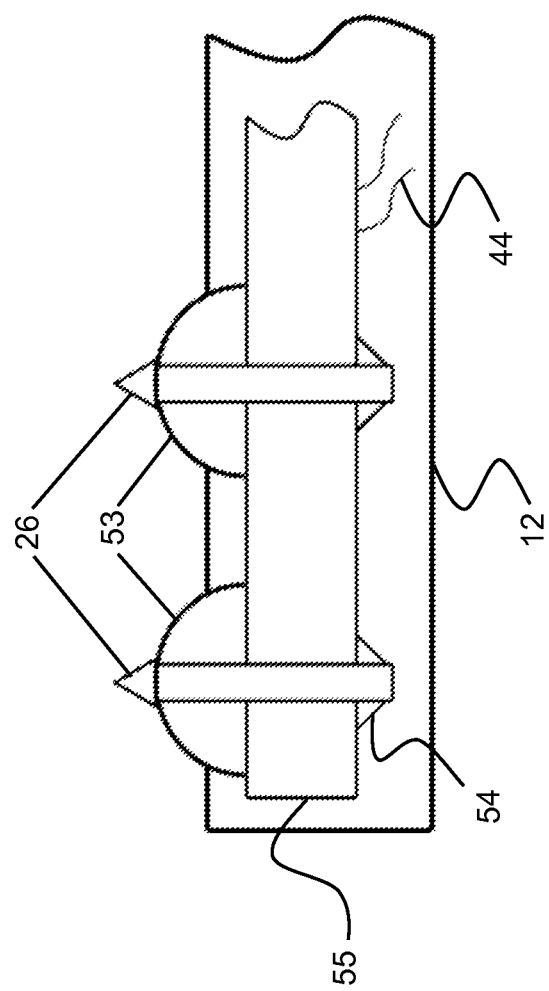

Having thus described the invention in general terms, reference will now be made to the accompanying drawings, which are not necessarily drawn to scale, and wherein:

FIG. 1. illustrates various components of a device for treating xerostomia with electro-stimulation, in accordance with an embodiment of the invention;

FIG. 2 illustrates a system for treating xerostomia where the device of FIG. 1 is connected to a lingual bar, in accordance with an embodiment of the invention;

FIG. 3 illustrates another system for treating dry mouth, where device of FIG. 1 is connected to a dental clasp, in accordance with an embodiment of the invention;

FIG. 4 is a chart depicting the results of the clinical trial conducted using electrostimulation to increase saliva secretion;

FIG. 5 illustrates another system with the inside blown out, where the device of FIG. 1 has an elongated bar structure to treat dry mouth, in accordance with en embodiment of the invention;

FIGS. 6A, 6B, 6C, 6D, and 6E illustrate another system for treating dry mouth, where the device of FIG. 1 has an elongated bar structure in form of a pen, in accordance with en embodiment of the invention;

FIG. 7 is simplified lateral view of the user holding the device having an elongated bar structure, in accordance with an embodiment of the invention;

FIG. 8 illustrates a system for treating dry mouth, where device is connected to a boil and bite mouthpiece, in accordance with an embodiment of the invention;

FIGS. 9A and 9B schematically illustrate a system to treat dry mouth, where the device has a clasp like structure and is sustained by a lingual bar, in accordance with an embodiment of the invention;

FIGS. 10A, 10B, 10C, 10D, 10E, 10F, and 10G illustrates multiple shapes of electrodes used in the device, in accordance with various embodiments of the invention; and FIG. 11 illustrates an exemplary cross section of an intra-oral end's assembly of the device, in accordance with an embodiment of the invention.

DETAILED DESCRIPTION OF THE INVENTION

The present invention is of a device and method which can be used for stimulating salivation. Specifically, the present invention can be used for stimulating salivation in cases of xerostomia. The main advantage of the present invention over the prior art is that the device according to the present invention is constructed and designed to be configured by providing a device for inducing salivation which can be inserted and removed freely and safely by the user into and from the oral cavity, to therefore eliminate the discomfort, risk, invasiveness and inconvenience associated with using the prior art devices.

The principles and operation of a device and method for stimulating salivation according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to drawings, FIG. 1 illustrates various components of a device 10 for treating xerostomia. Device 10 may be used in the oral cavity (partly or entirely) of a user. Device 10 includes a housing 12 that encloses an electronic module 14 and a power source 22. Housing 12 provides protection to electronic module 14 and power source 22 from the wetness or damage in the oral cavity. The operation of device 10 may be controlled remotely through a remote control 27. A receiver 17 of device 10 may receive the signals from remote control 27. The signals may be communicated by for example, but not limited to, infrared, Radio Frequency (RF), Bluetooth and so forth. For this purpose, electronic module 14 may be made of materials such as vinyl, silicone, acrylate, ceramic, polymers, metal, metal alloys or other dental material, or any combination thereof.

Device 10 can be used to provide stimulus in form of electric signals to the oral cavity and induce production of saliva from one salivary gland or more. Electronic module 14 includes a signal generator 20 that generates the electric signals for stimulating the salivary glands. Signal generator 20 produces electrical impulses that are delivered to the oral cavity through electrodes 26. The impulses may have intensity between one microampere and 1000 microamperes. Further, the impulses may have amplitude of about half to ten volts, a pulse width of about 1-1000 microseconds and a frequency of about 1-160 Hz. Moreover, the impulses may have uni-polar or bi-polar characteristics. Furthermore, signal generator 20 may produce the impulses based on pre-defined parameters. The predefined parameters may include, for example a current, voltage, frequency, polarity, and duty cycle of the impulses. The values of the predefined parameters may be pre-set or controlled by the user of device 10 by using keypad 29 and or the remote control. Moreover, the values may be stored in a memory 18 and controlled by electronic components such as a processor 16 of electronic module 14. A person skilled in the art will appreciate that the electronic components may include Application-Specific Integrated Circuit (ASIC) or other electronic components instead or along with processor 16. For example, the values provided by the user may be stored in memory 18, which are then controlled by processor 16 for driving signal generator 20. Power source 22 provides power to electronic module 14. Power source 22 may include one or more batteries, for example, a coin cell, primary battery or a rechargeable battery producing voltages in the range of 1.2 volts to 9 volts.

Electronic module 14 and/or power source 22 may be coated with a protective coating such as parylene, a conformal coating, such as silicone, anti-bacterial coating, silver, silver-oxide, dental resins, nano particles, or any combination thereof prior to embedding them in housing 12. As a result, the durability of the components is increased.

Device 10 includes a sensor 30 for sensing wetness level in the oral cavity. Thereafter, processor 16 may adjust the values of the parameters based on the wetness level. Memory 18 may include the operating rules for device 10, for example, the values of the parameters based on the wetness level. Therefore, processor 16 may take the values from the memory corresponding to the wetness level and control device 10 based on the predefined operating rules. Furthermore, device 10 includes a switch 24 to power on and power off device 10. Switch 24 is connected to electronic module 14 and/or power source 22.

Electrodes 26 may protrude from device 10 and contact the oral mucosa in the oral cavity. Therefore, electrodes 26 may provide electric stimulus to lingual nerves and induce salivation from salivary glands. The material of electrodes 26 may include bio-compatible material, for example, Nickel (Ni), Titanium (Ti) and Naval Ordnance Laboratory (NOL) (NiTiNol) or its alloys such as B, C, Dy70, Dy90, H, M, N, S, or stainless steel, platinum, platinum-iridium alloy, gold, silver, silver-oxide, titanium or polymers with memory. Further, the surface of electrodes 26 may be finished with for example, electropolish, coated with polymers, plated with gold, gold alloy, platinum-iridium alloy silver, nickel, platinum, silver, silver-oxide, copper, titanium oxide or any combination thereof. Electrodes 26 may be in form of a pair or an array. For example, the array may include array of about 100 electrodes 26. Furthermore, the inter-spacing between electrodes 26 may be pre-designed for effectiveness.

Device 10 may further include a display 28 for displaying information to the user. For example, the display be present the stimulation level, the value of the predefined parameters, and so forth. Display 10 may be for example, a Liquid Crystal Display (LCD), 7 segments display, 16 segments display, a Light Emitting Diode (LED) display, or any other type of display compatible with components of device 10.

Although not shown, a person skilled in the art will appreciate that device 10 may include further components such as LED lights, receiver for remote control, Printed Circuit Board (PCB), or combinations thereof.

Device 10 can be inserted and removed from the oral-cavity repeatedly by the user without the assistance from professional care giver. Therefore, device 10 is reusable. Further, the form factor of device 10 can be adapted to the oral cavities of multiple users. Therefore, the structure may not be modified or specially designed based on the characteristics of the oral cavities of the individual users. As a result, device 10 is easier to use, easier to manufacture, more comfortable and less costly as compared to already known devices for treating xerostomia. The various embodiments of the structures of device 10 are discussed in conjunction with the figures below.

Referring now to FIG. 2 illustrates a system 200 for treating xerostomia where device 10 is connected by a lingual bar 36, in accordance with an embodiment of the invention. In an embodiment of the invention, lingual bar 36 is positioned behind the teeth of the lower jaw (incisors 31, canines 32, pre-molars 33, first and second molars 34 and third molars or "wisdom teeth" 35, and underneath the tongue 38). Device 10*a* and 10*b* are connected to posterior ends of lingual bar 36 to treat dry mouth by electro-stimulation. Electrodes 26*a* and 26*b* protrude from device 10*a* and 10*b* respectively and contact oral mucosa 40.

Devices 10*a* and 10*b* are kept in place on the lingual side of the lower jaw by virtue of the lingual-bar structure. The spring like characteristics of lingual bar 36 pushes devices 10*a-b* and electrodes 26*a-b* to the lingual side and toward the inner part of the mouth (the distal part) and attach it to the gums. Moreover, the spring like property of lingual bar 36 enables system 200 to be adapted to oral cavities of multiple users without any modification. Moreover, the electro-stimulation of oral mucosa 40 may result in stimulation of lingual never for inducing saliva production from the salivary glands. Device 10*a-b* as shown here are connected to lingual bar 36, however, a person skilled in the art will appreciate that device 10 can have a structure in form of a lingual bar.

FIG. 3 illustrates a system 300 for treating dry mouth, where device 10 is connected to a dental clasp 43, in accordance with an embodiment of the invention. Clasp 43 is attached to a molar band 42. Molar band 42 can be previously positioned on a tooth. Clasp 43 holds device 10 to treat dry mouth by electro-stimulation. Electrodes 26 that protrude from device 10 contact the oral mucosa 40. Device 10 may be inserted or removed from the oral cavity by connecting or disconnecting from dental clasp 43. Therefore, system 300 can be adapted to oral cavities of multiple users without any modification. Moreover, the electro-stimulation of oral mucosa 40 may result in stimulation of lingual never for inducing saliva production from the salivary glands. Device 10*a-b* as shown here are connected to dental clasp 43, however, a person skilled in the art will appreciate that device 10 can have a structure in form to directly fit on molar band 42.

FIG. 4 is a chart 400 depicting the results of the clinical trial conducted using electrostimulation to increase saliva secretion by using an electrostimulating system similar to the presented herein. The results were conducted over a time of eight months. As shown, the percentage improvement in saliva secrection after one month was 5 percent, 32 percent after 5 months and 45 percent after 8 months.

FIG. 5 illustrates device 10 with few inside parts are blown out, where the structure of device 10 is in form of elongated bar structure to treat dry mouth. As shown, electrodes 26 can be connected to electronic module 14 through connectors 44. The connectors 44 can be for example, insulated metal wires that can conduct electric signals. Further, switch 24 may be used to switch on or switch off device 10, and display 16 may present a display to the user. Device 10 can be easily inserted or removed from the oral cavity of the user due to the elongated bar structure by using the extra-oral component 45. Extra-oral component 45 (here after referred to as handle 45) can be used to hold and maneuver device 10. Although, only a particular portion of device 10 is shown as handle 45, a person skilled in the art will appreciate that the length of handle 45 may encompass a small portion of device 10 or significant portion of device 10, depending on the position of the oral cavity of the user. Further, the electric stimulus can be provided at a desired location inside the oral cavity. Moreover, the elongated bar structure may be used for oral cavities of various users without re-designing or modifying device 10. Various other forms of elongated bar structure, with various angles between the intra-oral part and the extra-oral part are possible, some of which are discussed in conjunction with the figures below.

With reference to FIGS. 6A, 6B, 6C, 6D and 6E device 10 is illustrated having the structure in form of elongated bar such as a pen. As shown in FIGS. 6A, 6B, 6C, 6D and 6E device 10 can be carried by the user easily like a pen. Further, device 10 includes electrodes 26 that can be used to provide electric stimulation to the oral cavity of the user. Further, device 10 can be repeatedly inserted and removed from the oral cavity of the user by using handle 45. The use of handle 45 is illustrated with FIG. 7.

As shown in FIGS. 6A and 6B, switch 24 is located at a top end of the structure of device 10. Therefore, switch 24 is accessible from any angle with respect to electrodes 26. As a result, device 10 can be used to apply the electrical stimulus at various locations in the oral cavity. Further, device 10 can be used to stimulate the lingual nerves. Moreover, as shown in FIG. 6B, a curve 46 provides the user with further capabilities to maneuver device 10 in the oral cavity. In an embodiment of the invention, as shown in FIGS. 6C, 6D, and 6E, switch 24 is located on a side of the structure of device 10. A person skilled in the art will appreciate that switch 24 can be located on any side of device 10. Further, as shown in FIG. 6E, electrodes 26 can be covered by a protection cover 46 for hygiene and mechanical protection.

FIG. 7 is simplified lateral view of the user holding device 10 having an elongated bar structure, in accordance with an embodiment of the invention. As shown, handle 45 protrudes from the oral cavity of the user. Therefore, the user can operate device 10 by using handle 45. Further, controls such as display 28 and switch 24 (not shown) may be provided on handle 45 for operating device 10 by the user.

With reference to FIG. 8, a system 800 for treating dry mouth, where device 10 is connected to a boil and bite mouthpiece 48 made out from, for example, thermoplastic materials, in accordance with an embodiment of the invention. Mouthpiece 48 is adapted by the user jaws and teeth form factor by immersing it in hot water (until it becomes soft and pliable) and then placing it in their mouth to give its specific shape. The inner horizontal surface 49 faces the occlusal (chewing) surface of the lower teeth, the outer vertical surface 51 faces the labial/buccal (outer) surface of the lower teeth, and the inner vertical surface 50 faces the lingual (inner) surface of the lower teeth. Devices 10*a* and 10*b* are attached to mouthpiece 48 at posterior ends, to treat dry mouth by electro-stimulation. Electrodes 26*a* and 26*b* protrude from the devices 10*a* and 10*b* to contact the oral mucosa.

FIGS. 9A and 9B schematically illustrates a system 900 to treat dry mouth, where device 10 has a clasp like structure and sustained by a lingual bar 52. The flexibility of lingual bar 52 pushes the electrodes of device 10 towards the lingual (inner) side and to the distal (posterior) part, close to the third molar. Therefore, the electrodes may provide stimulus to lingual nerves.

FIGS. 10A, 10B, 10C, 10D, 10E, 10F, and 10G illustrate multiple shapes of electrodes 26 used in the device, in accordance with various embodiments of the invention. Electrodes 26 are connected to electronic module 14 to receive electric signals. As shown in FIG. 10A-G, various shapes of electrode 26 include, FIG. 10A—hook like, FIG. 10B—straight, FIG. 10C—mushroom like, FIG. 10D-a spring like electrode, FIG. 10E—dome like, FIG. 10F—'shock absorber' like, and FIG. 10G—'spider leg' like. The various shapes as illustrated may provide different effective stimulus to the oral cavity based on the type of shape. The suggested electrodes shapes provides some degree of structure flexibility for patient comfort, yet maintaining the distance between the electrodes to a pre-defined distance and pre-defined current density as defined by the contacting surface and current applied by the electronic module 14.

FIG. 11 illustrates an exemplary cross section of an intra-oral end assembly of device 10, in accordance with an embodiment of the invention. As shown, electrodes 26 are soldered 61 to Printed Circuit Board (PCB) 55. The tips of electrodes 26 protrude from housing 12. Further, connectors 44 may connect PCB 55 to electronic module 14.

Electrodes 26 (except the tips) may be covered with a soft material 53 cover, such as silicone, sponge, soft plastic and so forth. Therefore, the structure is comfortable to the user as electrodes 26 touch only at their tips. Moreover, the structure is durable as electrodes 26 are held firmly in their positions by soldering and electronic module 14 and power source 22 remain out of the intra-oral end of device 10.

Having discussed the exemplary embodiments the system and device 10 for treating dry mouth, it should be appreciated that a method of treating try mouth is also contemplated. A reusable intra-oral device for treating dry mouth or xerostomia is provided. The device includes a structure that is adaptable for oral cavities of multiple users. The device comprises a hermetically sealed housing and the housing includes an electronic module and power source. The electronic module includes a signal generator that generates electrical signals based on values of predefined parameters. Further, the device includes electrodes connected to the electronic module. The electrodes apply the electric signals for stimulating lingual nerves in the oral cavities to induce salivation. Further, the method includes placing the device in the oral cavities of the users. Thereafter, the user may operate the device by switching on or off from a switch. As a result, electrical signals in form of impulses are applied to stimulate the lingual nerves and induce saliva from the salivary glands.

While the invention has been described in connection with what is presently considered to be the most practical and various embodiments, it is to be understood that the invention is not to be limited to the disclosed embodiments, but on the contrary, is intended to cover various modifications and equivalent arrangements included within the spirit and scope of the appended claims.

This written description uses examples to disclose the invention, including the best mode, and also to enable any person skilled in the art to practice the invention, including making and using any devices or systems and performing any incorporated methods. The patentable scope the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A reusable device for treating xerostomia, the device having an extra-oral part and an intra-oral part, the intra-oral part having a structure adaptable for oral cavities of one or more users and being shaped as a lingual bar, the intra oral part having a spring like property, and configured to be insertable and removable by a user one or more times from the oral cavities, the device comprising:
   a housing comprising an electronic module having a signal generator configured to generate electrical signals based on one or more values of one or more predefined parameters, wherein the electrical signals comprise a series of pulses having an amplitude in the range of half to ten volts, a pulse width in the range of 1-1000 micro-seconds and a frequency in the range of 1-160 Hz;
   a plurality of electrodes connected to the electronic module, wherein the electrodes are configured to apply electric signals for stimulating lingual nerves in the oral cavities to induce salivation; and
   a switch connected to the electronic module, wherein the switch is configured to power on and power off the device, wherein the electronic module further comprises a power source configured to provide electric power to the device, and a processor configured to control the one or more values of the one or more predefined parameters.

2. The device of claim 1, wherein the electronic module further comprises a sensor configured to detect a wetness level of an oral cavity and set a stimulation level based on the wetness level.

3. The device of claim 1, wherein the electronic module further comprises a memory configured to store the one or more values of the one or more predefined parameters, and the memory is further configured to store a set of predefined operating rules.

4. The device of claim 1 further comprising an external remote control using infra red or RF communication to control the device.

5. The device of claim 1 further comprising of one or more keys or a keypad to input parameters to a memory of the device, wherein the one or more parameters comprise at least one of a current, voltage, frequency, and duty cycle.

6. The device of claim 1 further comprising a display connected to the electronic module, wherein the display is configured to present a stimulation level to the one or more users.

7. A method for treating xerostomia, the method comprising:
   placing a reusable device in oral cavity for treating xerostomia, the device, having an extra-oral part and an intra-oral part, the intra-oral part having a structure adaptable for oral cavities of one or more users and being shaped as a lingual bar, the intra oral part having a spring like property, and configured to be insertable and removable by a user one or more times from the oral cavities, the device comprising a housing, the housing comprising an electronic module having a signal generator configured to generate electrical signals based on one or more values of one or more predefined parameters, and a plurality of electrodes connected to the electronic module, wherein the electrodes are configured to apply electric signals for stimulating lingual nerves in the oral cavities to induce salivation.

8. The method of claim 7, wherein the electronic module further comprises a sensor configured to detect a wetness level of an oral cavity and set a stimulation level based on the wetness.

9. The method of claim 7, wherein the electronic module further comprises a memory configured to store the one or more values of the one or more predefined parameters, and the memory is further configured to store a set of predefined operating rules.

10. The method of claim 7, wherein the device further comprises an external remote control using infra red or RF communication to control the device.

11. The method of claim 7, wherein the device further comprises one or more keys or a keypad to input parameters to a memory of the_device, wherein the input parameters comprise at least one of a current, voltage, frequency, and duty cycle.

12. The method of claim 7 further comprising a display connected to the electronic module, wherein the display is configured to present a stimulation level to the one or more users.

13. A reusable intra-oral device for treating xerostomia, the device having a structure adaptable for oral cavities of one or more users, the device shaped as a lingual bar, having a spring like property, and configured to be insertable and removable by a user one or more times from the oral cavities, wherein the device comprises a plurality of electrodes, and wherein the electrodes are configured to apply electric signals for stimulating lingual nerves in the oral cavities to induce salivation.

14. The device of claim 13, further comprising:
   a housing comprising an electronic module having a signal generator configured to generate electrical signals with the plurality of electrodes, based on one or more values of one or more predefined parameters; and
   a switch connected to the electronic module, wherein the switch is configured to power on and power off the device,
   wherein the electronic module further comprises a power source configured to provide electric power to the device, and a processor configured to control the one or more values of the one or more predefined parameters, and
   wherein the electrical signals comprise a series of pulses having an amplitude of about half to ten volts, a pulse width of about 1-1000 micro-seconds and a frequency of about 1-160 Hz.

* * * * *